United States Patent [19]
Srivastava et al.

[11] Patent Number: 6,117,640
[45] Date of Patent: Sep. 12, 2000

[54] **RECOMBINANT VACCINE MADE IN *E. COLI* AGAINST DENGUE VIRUS**

[75] Inventors: Ashok Kumar Srivastava; J. Robert Putnak, both of Silver Spring; Charles H. Hoke, Columbia; Richard L. Warren, Brookville, all of Md.

[73] Assignee: The United States of America as represented by the Secretary of the Army, Washington, D.C.

[21] Appl. No.: 08/433,263

[22] Filed: May 2, 1995

[51] Int. Cl.[7] .......................... A61K 39/12; C07H 21/04; C07K 14/18

[52] U.S. Cl. .......................... 435/7.1; 435/7.9; 435/7.92; 435/69.1; 435/975; 424/186.1; 424/218.1; 436/536; 530/350; 536/23.4; 536/23.72

[58] Field of Search .............................. 424/186.1, 218.1; 435/69.1, 975, 7.1, 7.92, 7.9; 436/536; 530/350; 536/23.4, 23.72

[56] References Cited

FOREIGN PATENT DOCUMENTS

| | | |
|---|---|---|
| 9001946 | 3/1990 | WIPO . |
| 9202548 | 2/1992 | WIPO . |

OTHER PUBLICATIONS

Srivastava, A. K. et al. Japanese encephalitis virus fusion protein with protein A expressed in *Escherichia coli* confers protective immunity in mice. Microbiol. Immunol., 1991, 35: 863–870.

Srivastava, A. K. et al. Mice immunized with dengue–2 virus E and NS–1 fusion protein are protected against lethal dengue virus infection. Abstract, 43rd Annual Meeting of the American Society of Tropical Medicine and Hygiene, Sep. 1994, 51:437.

Ulmer, J. B. et al. Heterologous protection against influenza by injection of DNA encoding a viral protein. Science, 1993, 259: 1745–1749.

Acsadi, G. et al. Human dystrophin expression in mdx mice after intramuscular injection of DNA constructs. Nature, 1991, 352: 815–818.

Wolff, J. A. et al. Direct gene transfer into mouse muscle in vivo. Science, 1990, 247:1465–1468.

Zhang et al. J. Virol., 62(8), Aug. 1988, p. 3027–3031.

Mason et al. J. Gen. Virol., vol. 71, 1990, p 2107–2114.

Parrish et al. Arch. Virol., vol. 117, 1991, p 279–286.

Fonseca et al. Vaccine, 12(3), 1994, p 279–285.

Feighny et al. Amer. J. Trop. Med. and Hygiene. 50(3), 1994, p 322–328, Abstract.

Eckels et al. Amer. J. Trop. Med. and Hygiene.50(4). 1994, p 472–478.

*Primary Examiner*—Jeffrey Stucker
*Assistant Examiner*—Phuong T Bui
*Attorney, Agent, or Firm*—Charles H. Harris; John Francis Moran

[57] ABSTRACT

A recombinant protein encompassing a C-terminal protion from the structural envelope glycoprotein and an N-terminal portion from non-structural protein one of dengue type 2 virus was expressed in *Escherichia coli* as a fusion protein with Staphylococcal protein A. The recombinant protein was found to provide protection against lethal challenge with dengue 2 in mice.

4 Claims, 4 Drawing Sheets

RECOMBINANT VACCINE MADE IN *E. COLI* AGAINST DENGUE VIRUS

INTRODUCTION

Dengue (DEN) viruses are human pathogens with a significant threat to world health. These viruses are estimated to cause several hundred thousand cases of dengue fever, dengue hemorrhagic fever (DHF) and dengue shock syndrome (DSS) annually (Shope, R. E. In: *The Togaviruses.* Schlesinger, R. W. (Ed.) Academic Press, New York. 1980, pp. 47–82; Monath, T. P. In: *The Togaviridae and Flaviviridae,* Schlesinger, S. and Schlesinger, M. J. (Eds.) New York and London, 1986, pp. 375–440; Halstead, S. B. *Bull. W.H.O.* 1980, 58, 1–21; Halstead, S. B. *Am. J. Epidemiol.* 1984, 114, 632–648) (The complete content of all documents cited herein are hereby incorporated by reference). DEN viruses are members of the family flaviridae and are transmitted by Aedes mosquitoes (Halstead, S. B. *Science* 1988, 239,476–481). There are four serological types, DEN-1, DEN-2, DEN-3 and DEN-4, distinguishable by complement-fixation assays (Sabin, A. B. and Young, I. A. *Proc. Soci. Exp. Biol. Med.* 1949, 69, 291–296), virus plaque-reduction neutralization tests (Russell, P. K. and Nisalak, A. *J. Immunol.* 1967, 99, 291–296) and immunoassays using monoclonal antibodies (MAbs) (Gentry, M. K. et al. *Am. J. Trop. Med. Hyg.* 1982, 31, 548–555; Henchal, E.A. et al. *Am. J. Trop. Med. Hyg.* 1982, 31, 830–836).

DEN viruses are composed of a single-stranded RNA molecule of positive polarity (messenger sense) which is contained within a nucleocapsid composed of capsid (C) protein. The capsid is surrounded by a lipid envelope about 50 nm in diameter in which are embedded the envelope (E) glycoprotein and the matrix (M) protein. Both the structural and nonstructural (NS) proteins are encoded by a single, long open reading frame of about 10.5 kilobases arranged as follows: C-PreM/M-E-NS1-NS2A-NS2B-NS3-NS4A-NS5 (Rice, C. M. et al. *Science* 1985, 229, 726–733; Wengler, G. et al. *Virology* 1985, 147, 264274; Castle, E. et al. *Virology* 1986, 149, 10–26; Zhao, B. et al. *Virology* 1986, 155, 77–88; Mason, P. W. et al. *Virology* 1987, 161, 262–267; Mackow, E. et al. *Virology* 1987, 159,217–228; Sumiyoshi, H. et al. *Virology* 1987, 161,497–510; Irie, K. et al. *Gene* 1989, 74, 197–211).

Both the envelope (E) and the nonstructural protein 1 (NS1) are candidates for recombinant, subunit vaccines against DEN virus. The E glycoprotein is the major surface protein of the virion. It functions in virion attachment to host cells and it can be detected by its ability to hemagglutinate goose erythrocytes. As an antigen, it contains virus-neutralizing epitopes (Stevens, T. M. et al. *Virology* 1965, 27, 103–112; Smith, T. J. et al. *J. Virol.* 1970, 5,524–532; Rice, C. M. and Strauss, J. H. *J. Mol. Biol.* 1982, 154, 325–348; Brinton, M. A. In: *Togaviridae and Flaviridae.* Schlesinger, S. and M. J. Schlesinger (Eds.), M. J. Plenum, N.Y., 1986, pp. 327–365; Heinz, F. X. *Adv. Virus Res.* 1986,31,103–168; Westaway, E. G. *Adv. Virus Res.* 1987, 33,45–90; Hahn, Y. S. et al. *Arch. Virol.* 1990, 115, 251–265). Neutralizing antibodies, believed to correlate with protection, and hemagglutination-inhibiting (HI) antibodies develop following natural infection. Mice immunized with purified DEN-2 E antigen develop neutralizing antibodies and are protected against lethal virus challenge (Feighny, R. J. et al. *Am. J. Trop. Med. Hyg.* 1992, 47, 405–412). NS1 has also been shown to elicit a protective immune response in mice; however, this protection does not involve anti-virion antibodies (Schilesinger, J. J. et al. *J. Gen. Virol.* 1987, 68, 853–857; Henchal, E. A. et al. *J. Gen. Virol.* 1988, 69, 2101–2107).

Attempts to prevent DEN virus infection have focused on the production of a vaccine which would protect against all four serotypes. However, despite more than 50 years of effort, safe and effective dengue virus vaccines have not been developed. Candidate vaccines currently being tested fall into two categories: live attenuated dengue virus vaccines and subunit vaccines, each with its own drawbacks.

Live attenuated virus vaccines have been demonstrated to be either under-attenuated (cause disease) or over-attenuated (fail to immunize). Even an optimally-attenuated live virus vaccine can revert to a virulent (disease-causing) form through mutation. Live dengue viruses are also sensitive to heat, making it difficult and costly to maintain the vaccine in some tropical and subtropical countries where the vaccine may be needed most.

Recombinant subunit vaccines have the advantage of eliminating the risk of infectivity and greater chemical stability. However, the subunit vaccines of flavivirus structural and NS proteins produced in expression vectors including baculovirus, vaccinia virus and *E. coli* reported so far elicit only low titers of neutralizing antibody and are difficult to produce in large quantities and pure form (Putnak, J. R. et al. *Virology* 1988, 163, 93–103; Putnak, J. R. et al. *Am. J. Trop. Med. Hyg.* 1991, 45, 159–167; Zhang, Y. M. et al. *J. Virol.* 1988, 62, 3027–3031; Lai, C. J. et al. In: *Vaccines, Modern Approaches to New Vaccines Including Prevention of AID S* (Eds. Lerner, R. A. et al.), Cold Spring Harbor Laboratory Press, New York, 89, 1989, pp. 351–356; Bray, M. et al. *J. Virol.* 1989, 63, 2853–2856; Bray, M. and Lai, C. J. *Virology* 1991, 185, 505–508; Men, R. et al. *J. Virol.* 1991, 65, 1400–1407; Mason, P. W. et al. *Virology* 1987, 158, 361–372; Mason, P. W. et al. *J. Gen. Virol.* 1989, 70, 2037–2049; Mason, P. W. et al. *J. Gen. Virol.* 1990, 71, 2107–2114; Murray, J. M. et al. *J. Gen. Virol.,* 1993, 74, 175–182; Preugschat, F. et al. *J. Virol.* 1990, 64, 4364–4374). Baculovirus recombinants have been shown to confer protection against virus challenge but are membrane-associated, produced in low yields, and difficult to purify without denaturation. As crude immunogens they elicit little or no neutralizing antibody in mice, making them unlikely candidate vaccines. Similarly, a recombinant protein containing the C-terminus of the E protein from Japanese encephalitis (JE) virus, another flavivirus, fused with TrpE protein (tryptophan synthetase E protein) and expressed in *E. coli* produced high levels of recombinant protein and was recognized by JE-neutralizing monoclonal antibodies in Western blot assays. However, this recombinant protein formed insoluble, intracellular inclusion bodies and required detergents for its purification.

Therefore, in view of the problems with the presently available vaccines discussed above, there is a need for a dengue vaccine that elicits very high titers of neutralizing antibody, provides protection against the disease, has no possibility of infectivity to the immunized host, can be produced easily in pure form, and is chemically stable.

SUMMARY

The present invention is directed to a recombinant dengue virus subunit vaccine that satisfies this need. The recombinant dengue virus subunit vaccine of the present invention comprises a part of the envelope (E) protein and a part of nonstructural 1 (NS1) protein. This recombinant protein product is produced in *E. coli* in large quantities and in pure form, elicits high titers of neutralizing antibody and is protective against the disease in the immunized animal.

The present invention describes the production of a fusion protein containing the carboxy-terminus of E protein and the amino-terminus of NS1 protein by cloning the complimentary DNA (cDNA) sequences encoding these protein fragments into an expression vector such that the recombinant dengue protein can be expressed as a fusion protein with Staphylococcal protein-A. The recombinant protein is produced in E. coli, isolated and purified. The recombinant protein is shown to be antigenic, reactive with dengue virus-specific polyclonal and monoclonal antibodies and capable of eliciting the production of neutralizing antibodies when inoculated into mice. The administration of this recombinant subunit vaccine is demonstrated to protect mice, an accepted animal model, against morbidity and mortality following challenge with live dengue virus.

Therefore, it is an object of the present invention to provide a dengue 2 cDNA fragment extending from nucleotide 1801 to nucleotide 2615 of the viral genome sequence which encodes the carboxy-terminal 204 amino acids of E protein and the amino-terminal 65 amino acids of NS1 and is useful as a diagnostic agent and a naked DNA vaccine.

It is another object of the invention to provide a recombinant vector designed to produce the recombinant dengue protein for use as a vaccine and as a diagnostic agent.

It is still another object of the invention to provide a purified recombinant dengue 2 recombinant protein useful as a vaccine against dengue 2 disease and for detecting the presence of said disease in a suspected patient.

It is yet another object of the invention to provide a dengue virus vaccine effective for the production of antigenic and immunogenic response resulting in the protection of an animal against dengue virus disease.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
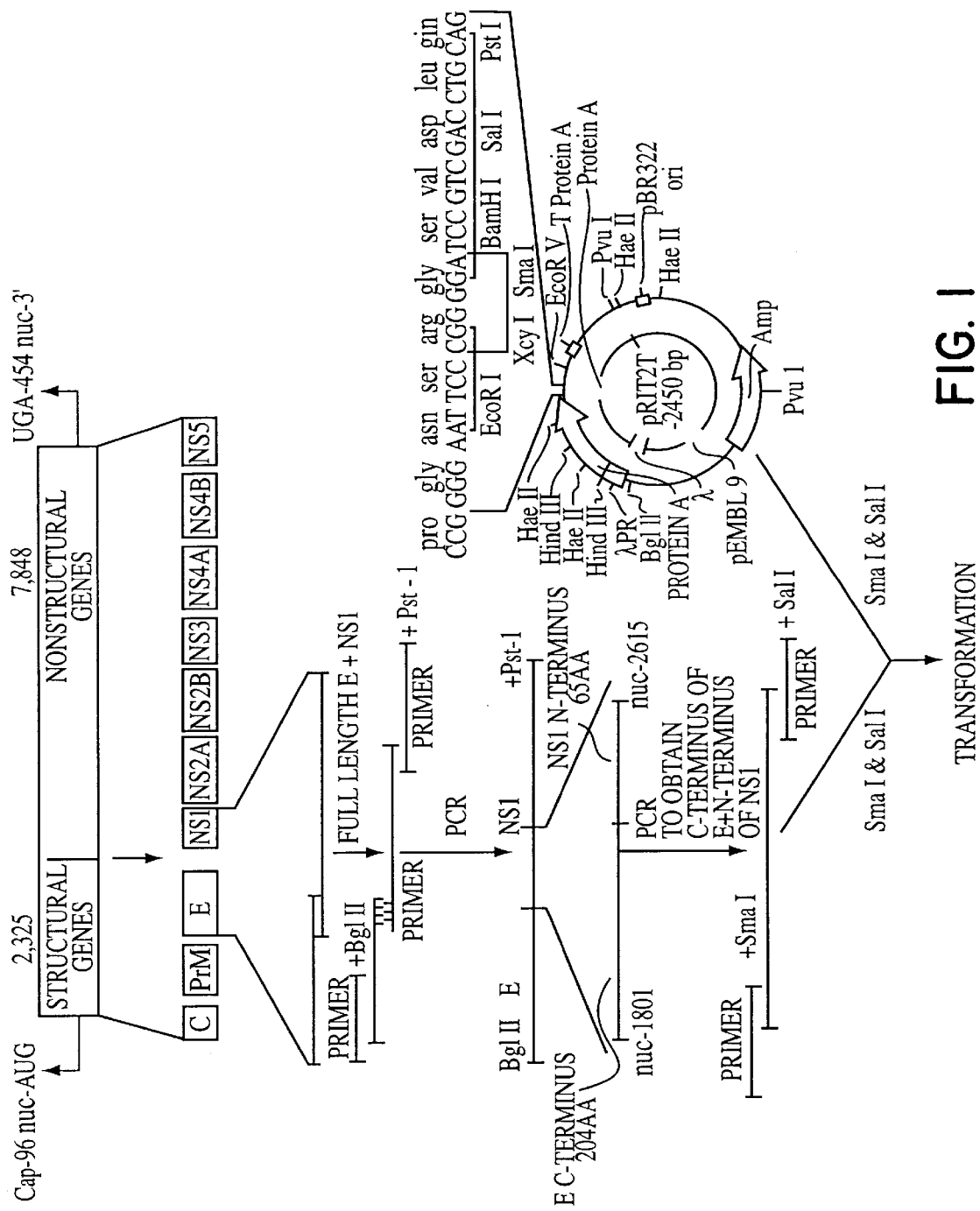
FIG. 1 demonstrates the construction of recombinant expression plasmid pRIT2T-#3A. A cDNA fragment corresponding to DEN-2 virus genome (nt-1801 to nt-2615, SEQ ID NO: 1) was obtained by the polymerase chain reaction (PCR) and inserted into the multiple cloning site in the protein A gene of pRIT2T under control of thermo-sensitive lambda phage repressor. In this construct the protein A gene was upstream of the insert.

In one embodiment, the present invention relates to a DNA or cDNA segment which encodes the carboxy terminal of the E protein and the amino terminal of the NS1 protein of dengue 2 extending from nucleotide 1801 to 2615 of the dengue 2 viral genome and including linear, neutralizing epitopes said sequence identified as SEQ ID NO: 1.

DNA sequences to which the invention also relates include sequences which encode the specific protein epitopes contained within said sequence which elicit neutralizing antibody production in animals upon administration of the protein encoded by said DNA sequences. Specifically, such sequences include regions encoding neutralizing epitopes present on the N-terminus of NS-1 protein (Putnak et al. Virology 1988, 163, 93–103; Young and Falconer, Proceedings of the Fifth Symposium Arbovirus Research in Australia, 1990, p. 62–67; Henchal et al, J. Gen. Virol. 1988, 69, 2101–2107) and the nucleotide sequence encompassing amino acids 384 through 396 of the E protein, this region specifically containing a recognition site for at least one anti-DEN-2 monoclonal antibody, for example, 3H5 (Trirawatanapong et al. Gene 1992, 116, 139–150).

In another embodiment, the present invention relates to a recombinant DNA molecule that includes a vector and a DNA sequence as described above (advantageously, a DNA sequence encoding the protein having the neutralizing antibody-eliciting characteristics of that protein). The vector can take the form of a virus such as, for example, bacculovirus vectors pBlueBac-III, pBlueBac-HIS-A-B-C, Mac-Bac; a plasmid, or eukaryotic expression vector such as GST gene fusion vectors, pGEx-3x, pGEx-2T, pGEx, pgex-1% λ/EcoRI and others known to people in the art. The DNA sequence can be present in the vector operably linked to regulatory elements, including, for example, a promoter or a highly purified human IgG molecule, for example Protein A, an adjuvant, a carrier, or an agent for aid in purification of the antigen. The recombinant molecule can be suitable for transforming prokaryotic cells, for example, E. coli, or transfecting eukaryotic cells for example, mammalian cells such as VERO or BHK cells, or insect cells such as Sf9 (Spodopter frugiperda) and C6/36 (Aedes albopictus) mosquito cells, among others.

In another embodiment, the present invention relates to a recombinant protein having an amino acid sequence corresponding to SEQ ID NO: 2 and encompassing 204 amino acids of the carboxy-terminal of E protein and 65 amino acids of the amino-terminal of NS1 protein from DEN-2 or any allelic variation thereof which maintains the neutralizing antibody production characteristic of the recombinant protein. As an example, the protein (or polypeptide) can have an amino acid sequence corresponding to an epitope such as a B-cell and T-cell epitope present on E or NS1 domains of dengue-2, or a linear neutralizing epitope contained in amino acids 384–396 of E protein, which has a recognition site for at least one anti-DEN-2 neutralizing monoclonal antibody, for example 3H5 (Gentry, M. K. et al. Am. J. Trop. Med. Hyg. 1982, 31, 548–555; Henchal, E. A. et al. Am. J. Trop. Med. Hyg. 1982,31, 830–836; Trirawatanapong et al. Gene, 1992, 116, 139–150). In addition, the protein or polypeptide can be fused to other proteins or polypeptides which increase its antigenicity, thereby producing higher titers of neutralizing antibody when used as a vaccine. Examples of such proteins or polypeptides include any adjuvants or carriers safe for human use, such as aluminum hydroxide.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). For instance, transient or stable transfections can be accomplished into CHO or Vero cells. Transformation or transfection can be accomplished using protocols and materials well known in the art. The transformed or transfected host cells can be used as a source of the DNA sequences described above. When the recombinant molecule takes the form of an expression system, the transformed or transfected cells can be used as a source of the above-described recombinant or fusion protein.

In a further embodiment, the present invention relates to a method of producing the recombinant or fusion protein which includes culturing the above-described host cells, under conditions such that the DNA fragment is expressed and the recombinant or fusion protein is produced thereby. The recombinant or fusion protein can then be isolated using methodology well known in the art. The recombinant or fusion protein can be used as a vaccine for immunity against infection with flaviviruses or as a diagnostic tool for detection of viral infection.

In another embodiment, the present invention relates to antibodies specific for the above-described recombinant proteins (or polypeptides). For instance, an antibody can be raised against a peptide having the amino acid sequence of SEQ ID NO: 2, or against a portion thereof of at least 10 amino acids, perferrably, 12–15 amino acids. Persons with ordinary skill in the art using standard methodology can raise monoclonal and polyclonal antibodies to the protein (or polypeptide) of the present invention, or a unique portion thereof. Material and methods for producing antibodies are well known in the art (see for example Goding, in, *Monoclonal Antibodies: Principles and Practice,* Chapter 4, 1986).

In a further embodiment, the present invention relates to a method of detecting the presence of dengue virus disease or antibodies against dengue virus in a sample. Using standard methodology well known in the art, a diagnostic assay can be constructed by coating on a surface (i.e. a solid support) for example, a microtitration plate or a membrane (e.g. nitrocellulose membrane), all or a unique portion of the recombinant or fusion protein described above, and contacting it with the serum of a person suspected of having dengue fever. The presence of a resulting complex formed between the recombinant or fusion protein and antibodies specific therefor in the serum can be detected by any of the known methods common in the art, such as fluorescent antibody spectroscopy or colorimetry. This method of detection can be used, for example, for the diagnosis of dengue disease.

In addition, the present invention is related to a method of detecting flavivirus disease or antibodies against flavivirus in a sample. Dengue viruses are members of the family flaviridae which includes over sixty members among which there is considerable genetic and antigenic similarity but no significant cross-neutralization. It would be apparent to persons in the art to apply the concepts of the present invention exemplified in dengue 2 to similar proteins and DNA sequences present in other related flaviviruses.

In another embodiment, the present invention relates to a diagnostic kit which contains the recombinant or fusion protein and ancillary reagents that are well known in the art and that are suitable for use in detecting the presence of antibodies to flavivirus antigens in serum or a tissue sample, specifically antibodies to dengue virus. Tissue samples contemplated can be monkey and human, or other mammals.

In another embodiment, the present invention relates to a vaccine for protection against a flavivirus disease. The vaccine can be prepared by inducing expression of the recombinant expression vector described above in either a prokaryotic or eukaryotic host and purifying the recombinant or fusion protein described above. The purified solution is prepared for administration to mammals by methods known in the art, which can include filtering to sterilize the solution, diluting the solution, adding an adjuvant and stabilizing the solution. The vaccine can be lyophilized to produce a flavivirus vaccine in a dried form for ease in transportation and storage. Further, the vaccine may be prepared in the form of a mixed vaccine which contains the recombinant protein described above and at least one other antigen as long as the added antigen does not interfere with the effectiveness of the dengue vaccine and the side effects and adverse reactions are not increased additively or synergistically. It is envisioned that a tetravalent vaccine composed of recombinant antigenic proteins from the four serotypes of dengue virus, DEN-1, DEN-2, DEN-3, and DEN-4 can be produced to provide protection against dengue disease.

The vaccine may be stored in a sealed vial, ampoule or the like. The present vaccine can generally be administered in the form of a liquid or suspension. In the case where the vaccine is in a dried form, the vaccine is dissolved or suspended in sterilized distilled water before administration. Generally, the vaccine may be administered subcutaneously, intradermally or intramuscularly in a dose effective for the production of neutralizing antibody and protection from infection.

In another embodiment, the present invention relates to a naked DNA vaccine. The dengue DNA fragment of the present invention described in SEQ ID NO: 1 or a portion thereof, or an allelic form thereof, can be administered as a vaccine to protect against dengue virus disease and to elicit neutralizing antibodies against the virus. It is understood and apparent to a person with ordinary skill in the art that due to the similarity between different serotypes of dengue as well as similarities between flaviviruses, a DNA sequence from any dengue serotype or flavivirus encoding the carboxy terminal region of E protein and the amino terminus region of NS1 of its respective flavivirus can be used as a naked DNA vaccine against infection with its respective virus. The dengue 2 naked DNA vaccine can be injected alone, or combined with at least one other antigen or DNA fragment as long as the added antigen or DNA fragment does not interfere with the effectiveness of the dengue vaccine and the side effects and adverse reactions are not increased additively or synergistically. It is envisioned that a tetravalent vaccine composed of DNA fragments from the four serotypes of dengue virus, DEN-1, DEN-2, DEN-3, and DEN-4 can be produced to provide protection against dengue disease.

The naked DNA vaccine of the present invention can be administered for example intermuscularly, or alternatively, can be used in nose drops. The DNA fragment or a portion thereof can be injected as naked DNA, as DNA encapsulated in liposomes, as DNA entrapped in proteoliposomes containing viral envelope receptor proteins (Nicolau, C. et al. *Proc. Natl. Acad. Sci. U.S.A.* 1983, 80, 1068; Kanoda, Y., et al. *Science* 1989, 243, 375; Mannino, R. J. et al. *Biotechniques* 1988, 6, 682). Alternatively, the DNA can be injected along with a carrier. A carrier can be a protein or such as a cytokine, for example interleukin 2, or a polylysine-glycoprotein carrier (Wu, G. Y. and Wu, C. H. *J. Biol. Chem.* 1988, 263,14621), or a nonreplicating vector, for example expression vectors containing either the Rous sarcoma virus or cytomegalovirus promoters. Such carrier proteins and vectors and methods for using same are known to a person in the art (See for example, Acsadi, G. et al. *Nature* 1991, 352, 815–818). In addition, the DNA could be coated onto tiny gold beads and said beads introduced into the skin with, for example, a gene gun (Cohen, J. *Science* 1993, 259, 1691–1692; Ulmer, J. B. et al. *Science* 1993, 259, 1745–1749).

Described below are examples of the present invention which are provided only for illustrative purposes, and not to limit the scope of the present invention. In light of the present disclosure, numerous embodiment within the scope of the claims will be apparent to those of ordinary skill in the art.

The following MATERIALS AND METHODS were used in the examples that follow.

Cell Culture and Virus

The C6/36 *Aedes albopictus* cell clone was grown and maintained as described previously (Srivastava, A. K. et al. *Arch. Virol.* 1987, 96, 96–107; Srivastava, A. K. et al. *Acta Virol* 1990,34, 228–238; Srivastava, A. K. et al. *Trop. Med.* 1990, 34, 228–238; Igarashi, A. *J. Gen. Virol* 1987, 40,531–544.). Clarified cell culture supernate fluid harvested from C6/36 cells infected with DEN-2 virus (New Guinea C) strain was used as stock virus.

Construction of Expression Plasmid

A full length cDNA fragment (PR-159-S1-vaccine strain) (Hahn, Y. S. *Virology* 1988, 162, 167–180) comprised of B and NS1 genes was made by polymerase chain reaction (PCR). The envelope (E) glycoprotein gene (nucleotide 844-2438) was amplified by PCR using specific primers (5'-TGACAGATCTATGATGGCCGAC ATCCGTGCA-3', nucleotide 844-874, SEQ ID NO: 3) and (5'-GGGAGTTATGGTG CAGGCCGATAGTGGTTGCGTTGT-3', nucleotide 2403-2438, SEQ ID NO: 4). The NS1 gene (nucleotide 2416-3660) was amplified separately using specific primers (5'-GCAGGCCGATAGTGGTTGCGTTGT-3', nucleotide 2416-2439, SEQ ID NO: 5) and (5'-TACTGCAGTTAACCCACCATAACCATCAC-3', nucleotide 3632-3660, SEQ ID NO: 6). Amplification was carried out in a 100 μl reaction containing 50 mM KCl, 10 mM Tris-HCl pH 8.3, 1.5 mM $MgCl_2$, and 0.5 picomoles of each primer, 100 ng of template DNA, 250 μM deoxynucleotide triphosphates (dNTPs) and 2.5 units of Taq polymerase (Perkin-Elmer Cetus Corp., Norwalk, Conn.). PCR was performed in an automated programmable thermal cycler (Perkin Elmer Model 9600). DNA was first denatured at 94° C. for 1 minute, this was followed by 20 cycles of annealing at 45° C. for 1 minute, extension at 72° C. for 4 minutes, and denaturation at 94° C. for 1 minute. A final extension was performed at 72° C. for 10 minutes. A 10 μl aliquot of PCR product was analyzed by electrophoresis on a 1% agarose gel (Sigma, St. Louis, Mo.). The resulting fragments were annealed by virtue of their overlap and then covalently joined using primers which anneal to the 5' end of NS1 (5'-ACAACGCAACCACTATCG GCCTGCACCATAACTCC-3', SEQ ID NO: 7) and the 3' end of E (5'-GCAG GCCGATAGTGGTTGCGTTGT-3', SEQ ID NO: 8) using reaction conditions described above except that only 10 cycles were used. This reaction resulted in a full length E and NS1 fragment. Finally, this fragment was used as template to amplify the region from nucleotide 1801 to 2615 using primers (5'-CCCGGGATGATGGACAAA TTACAACTT-3', SEQ ID NO: 9) and (5'-GTCGACTTAATTTTCCAGTCT TGTCAT-3', SEQ ID NO: 10) which also contained SmaI and SalI sites. PCR amplification was carried out as described above using 20 cycles. The resulting PCR fragment was digested with SmaI and SalI and ligated into the SmaI and SalI sites of a plasmid vector, pRIT2T (Nilson, B. et al. *EMBO J.* 1985,4, 1075–1080; Lowenadler, B. et al. *EMBO J.* 1986, 5, 2393–2398), purchased from Pharmacia LKB Biotechnology, Piscataway, N.J., (FIG. 1). This vector contains a truncated portion of the Staphylococcal Protein A gene under control of the λPR promoter. The plasmid with insert was designated pRIT2T-#3A. The correct orientation of the DEN cDNA insert was confirmed by restriction endonuclease digestion and DNA sequencing (Manniatis, T. et al. Molecular cloning:*A Laboratory Manual.* Cold Spring Harbor Laboratory, Cold Spring Harbor, N.Y., 1982).

DNA Sequencing

The DNA sequences were determined by a modification of dideoxynucleotide chain-termination reaction sequencing (Sanger, F. *Proc. Natl. Acad. Sci. U.S.A.* 1977, 74, 5463–5467), using florescence-labeled dideoxynucleotides with a Model 373A DNA sequencer (Applied Biosystems, Inc, Foster, Calif.). The fluorescence-based dideoxy sequencing reactions were carried out with Prism Cycle sequencing kits. One ml of a 40 pmol/μl stock of oligonucleotide primer 5'-GTCCAAGTTTCCCTG-3', SEQ ID NO: 11, or 5'-AATGATAACCATCTCGC-3', SEQ ID NO: 12, and 1–5 μg of target DNA were added to premixed cycle sequencing chemicals. The reaction mixture was heated to 96° C. for 1 minute, annealed at 50° C. for 30 seconds and extended at 60° C. for 4 minutes for a total of 25 cycles with a Perkin Elmer Thermocycler (model 9600). The unincorporated dye-labeled dideoxynucleotides were removed by centrifugation with Centri-Sep spin columns (Princeton Separation, Inc, Adelphia, N.J.). Sequencer 2.0 software (Gene Corp., Mich.) was used to analyze the sequence data.

Preparation of Fusion Protein

Recombinant plasmids were introduced by $CaCl_2$ transformation into *E. coli* N4830-1 (Pharmacia, Piscataway, N.J.) which contains the temperature-sensitive λcI857 repressor. Cells, selected from an ampicillin-resistant colony were grown at 29° C. overnight in Luria-Bertani broth containing 50 μg/ml ampicillin. The overnight culture was then diluted to 2-fold with the same medium and the temperature was shifted to 42° C. for 90 minutes. The cells were collected by centrifugation, resuspended in Tris-saline Tween-20 buffer (TST, 50 mM Tris, pH 7.6, 150 mM NaCl, 0.05% tween-20) to ¹⁄₁₀ the original volume and lysed by 2 passes through a French Press. The lysate centrifuged at 10,000 rpm in a Beckman type 30 rotor for 30 minutes at 4° C. The supernatant was centrifuged in a Beckman SW 41 rotor at 20,000 rpm for 60 minutes at 4° C. The resulting supernatant was applied to a IgG-Sepharose 6 column (Pharmacia, Piscataway, N.J.) as recommended by the manufacturer with some modifications. The negative control was similarly prepared from *E. coli* transformed with the pRIT2T plasmid without a DEN cDNA insert.

Sodium Dodecyl Sulfate Polyacrylamide Gel Electrophoresis (SDS-PAGE) and Western Blotting Proteins were solubilized in SDS-PAGE sample buffer containing 1% SDS, 66 mM Tris-HCl pH 6.8, 1% glycerol and 0.7% bromophenol blue at room temperature for 10 minutes. The samples were subjected to PAGE on 10% gels as described by Laemmli (Laemmli, U. K. *Nature* 1970, 227, 680–685). Protein bands were visualized by staining with 0.1% Comassie Brilliant Blue R-250 in 10% acetic acid and 30% methanol followed by destaining with 10% aceteic acid and 30% methanol.

Protein from the SDS-PAGE were electrophoretically transferred onto nitrocellulose membrane as previously described (Towbin, H. et al. *Proc. Natl. Acad. Sci. USA* 1979, 76, 4350–4354) with some modification. The transfer was performed in buffer containing 25 mM Tris, 125 mM glycine, 20% methanol and pH 8.3, at 4° C. for overnight at 8–10 V/cm in an transfer box, model TE-50 (Hoefer Scientific Instruments, SanFrancisco). The nitrocellulose membrane was briefly rinsed in deionized water and was blocked with 3% Casein in PBS (phosphate buffered saline) containing 0.01% $NaN_3$ for 45 minutes at room tempearature. The membrane was washed 3 times in PBS and reacted with anti-DEN-2 hyperimmune mouse ascitic fluid (HMAF) at a 1:500 dilution or anti-DEN-2 mouse monoclonal antibodies at a 1:1000 dilution in PBS containing 0.01% $NaN_3$ at 37° C. for 3 hours. The membrane was washed as above and reacted with peroxidase-conjugated goat anti-mouse IgG (Sigma, St. Louis, Mo.) at a 1:4000 dilution in PBS at 37° C. for 2 hours. The membrane was washed as above and the antigenically reactive protein bands were visualized by incubation with substrate solution (0.03% 4-chloro-1-naphthol and 0.03% $H_2O_2$ in PBS) at room temperature until color development was complete.

Immunological Reagents

DEN-2 HMAF was prepared as previously described (Brandt, W. E. et al. *Am. J. Trop. Med. and Hyg.* 1967, 16, 339–347; Chiewslip, D. and McCown, J. M. *Appl. Microbiol.* 1972, 24, 288–289). The DEN-2 specific mouse MAbs used in this study have previously been characterized. E antigen-specific (3H1, 4H7, 2H3, 3G11, 3H5) and NS1 antigen-specific (7E11) MAbs were used to demonstrate the antigenic specificity of the recombinant fusion protein.

Mouse Immunizations

The immunogenicity of the recombinant fusion protein was assayed in 5–6 week-old, genetically outbred, Swiss ICR mice which may be expected to respond well to most antigens. The mouse protection (virus challenge) assay was performed in 3 week old BALB/C mice (Charles River, N.Y.) because this strain shows high susceptibility to DEN 2 virus challenge but older mice become naturally-resistant to virus. All mice were immunized subcutaneously (SC) at the base of the tail with purified recombinant fusion protein (5 μg per dose), or with protein-A alone (5 μg per dose, negative control), or with live DEN-2 virus (one million PFU, positive control). Immunogen preparations were mixed (1:1) with either Hunter's TiterMax adjuvant (HTM) (Bennet, B. et al. *J. Immunol. Methods* 1992, 153,31–40), 0.1% aluminum hydroxide (AH) (April, M. A. and Wardlaw, A. C. *Can. J. Publ. Hlth.* 1966, 57, 343–360; Butler, N. R. et al. *Br. Med. J.* 1969, 1, 663–666; Kasel, J. A. et al. *J. Immunol.* 1971, 107, 916–919; Nicklas, W. *Res. Immunol.* 1992, 143, 489–494) or phosphate buffered saline (PBS). For both immunogenicity and protection assays mice were inoculated 4 times at 1 week intervals. Three days after the last inoculation blood was obtained by retro-orbital puncture. Sera were assayed for N and HI antibodies as described below. For virus protection experiments, mice were injected intracranially (IC) with 30 μl of a 20% suspension of DEN-2 (New Guinea C) virus-infected suckling mouse brain containing 100 50% lethal doses ($LD_{50}$). Mice were observed daily for 20 days for morbidity and mortality.

Hemagglutination Inhibition (HI) and Plaque Reduction Neutralization Tests (PRNT)

HI tests were performed essentially as previously described (Clarke, D. H. and Casals A. *J. Am. J. Trop. Med. Hyg.* 1958, 7, 561–573). The PRNT test was done using Vero cell monolayers in plastic 6-well plates (Coster, Cambridge, Mass.) and the New Guinea C strain of DEN-2 virus. The percent reduction of plaques (80% endpoint) was calculated by comparison with plaques obtained from virus mixed with negative control mouse sera.

EXAMPLE 1

Figure 2A:
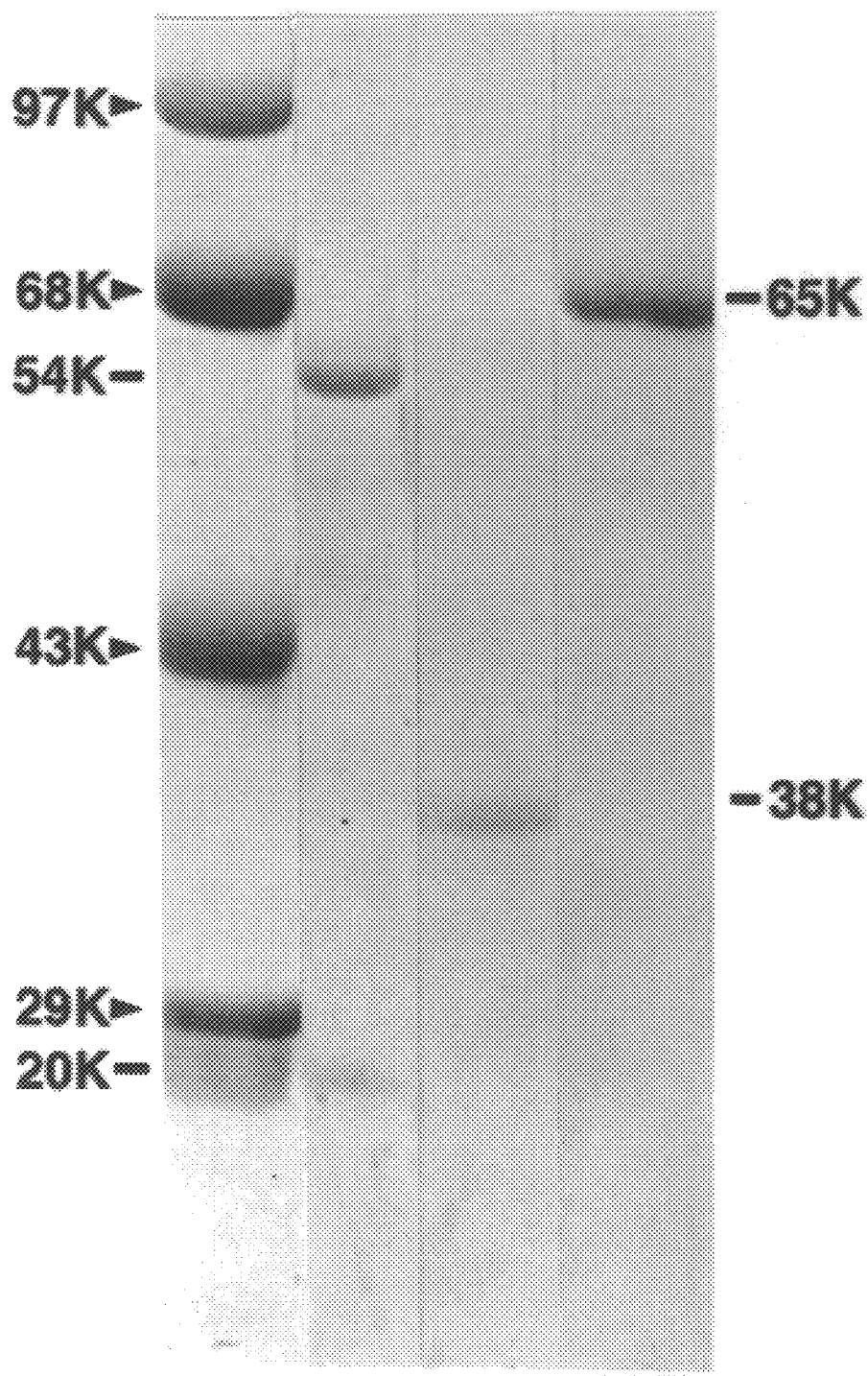
FIG. 2 shows the antigenicity of the recombinant fusion protein. Fusion protein was purified and electrophoresed on polyacrylamide SDS gels. Separated proteins were transferred to nitrocellulose and reacted with DEN-2 specific mouse hyperimmune ascitic fluid (MHAF) (right panel, 2b). Proteins from another gel were stained with Coomassie blue (left panel, 2a). Panel 2a: lane 1, marker; 2, Purified DEN-2 virus; 3, protein A and 4, recombinant fusion protein. Panel 2b: lane 1, Purified DEN virus; 2, protein A and 3, recombinant fusion protein.
Figure 2B:
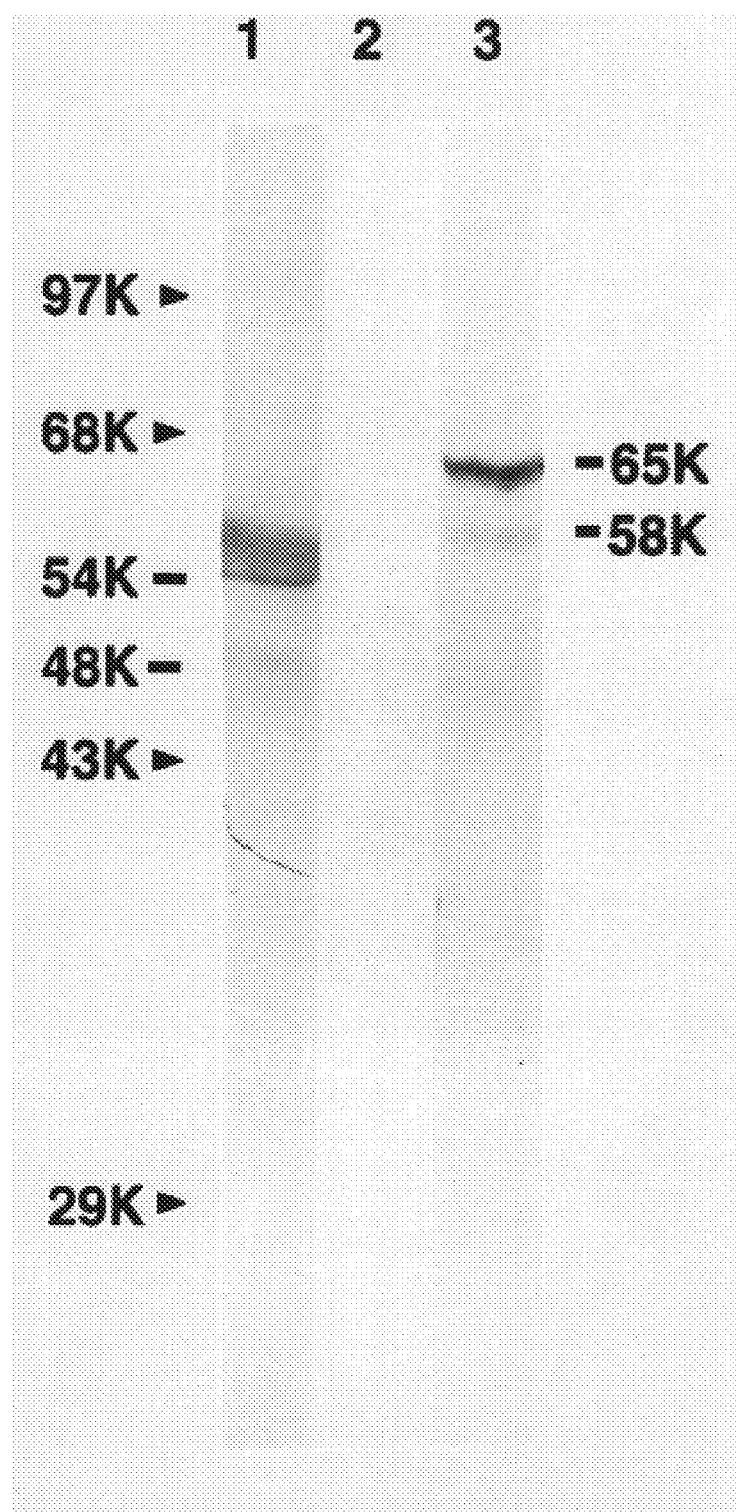

Production in *E. coli,* Purification and Characterization of Truncated DEN-2 Recombinant E-NS1 Protein Fused to Staphylococcal Protein A A DEN-2 cDNA fragment which encodes the C-terminus of E protein and the N-terminus of NS1 was cloned into an expression plasmid (pRIT2T) as shown in FIG. 1. The resulting plasmid (pRIT2T-#3A) encodes 204 AA from the C-terminus of E protein and 65 AA from the N-terminus of NS1 protein which are fused to the C-terminus of the Staphylococcal protein-A gene of the vector. Proteins were obtained from *E. coli* (strain N4830-1) transformed with pRIT2T-#3A or pRIT2T. The proteins were purified by affinity chromatography on an IgG-Sepharose column, then electrophoresed on polyacrylamide-SDS gels and stained with Coomassie blue (FIG. 2-*a,* left panel) or transferred to nitrocellulose paper and reacted with DEN-2 specific polyclonal antibody (HMAF) in a Western blot assay (FIG. 2-*b,* right panel). In the Western blot assay an antigenic protein of approximately 65 kilo-Daltons (kD), consistant with the combined size of the protein-A moiety (38 kD) and the truncated DEN E-NS1 protein (27 kD), was observed. A minor antigen (58 kD) which may be a degradation product of the full-length fusion protein was also seen (FIG. 2-*b,* right panel, lane 3). The recombinant protein also reacted in a Western blot assay with several E MAbs and one NS1 MAb (see Materials and Methods, data not shown). In the Coomassie blue-stained gel a single protein of 65 kD was seen (FIG. 2-*a,* left panel, lane 4) consistent in size with the intact fusion protein. The amount of fusion protein produced was approximately 8–10 mg per liter of cells estimated by determining the absorbance at 280 nm by spectrophotometry.

EXAMPLE 2

Immunogenicity of the Recombinant Fusion Protein in Mice

The purified, recombinant fusion protein was evaluated for its immunogenicity in mice. Outbred, Swiss ICR mice, 5 to 6 weeks old, were immunized with purified recombinant protein (3 mice), purified protein-A (3 mice), or live DEN-2 virus (3 mice). Four inoculations each containing 5 mg of protein in various adjuvants were given at one week intervals. Individual sera obtained 3 days after the final inoculation were tested for HI antibodies and pooled sera were tested for neutralizing antibodies (see Table 1). Neutralizing antibody titers, measured by virus plaque reduction neutralization (PRNT-80%) assay, were 1:320 with HTM adjuvant, 1:300 with AH adjuvant and 1:80 without adjuvant. HI antibody titers ranged from 1:320–1:640 with HTM, 1:160–1:1280 with AH and 1:80–1:320 without adjuvant. Similar titers were obtained with sera from mice immunized with live DEN-2 virus. Mice immunized with protein-A with or without adjuvant made no detectable anti-DEN-2 virus neutralizing or HI antibodies. Sera from mice immunized with recombinant antigen also reacted with authentic DEN-2 viral proteins in a Western blot assay (data not shown).

TABLE 1

Anti-DEN-2 HI and N antibody titers in sera from mice immunized with recombinant, protein A and DEN-2 virus

| Adjuvant[c] | | HTM | | | AH | | NONE | |
|---|---|---|---|---|---|---|---|---|
| Immunogen | Mouse number | HI[a] | PRNT[b] | Mouse | HI | PRNT | HI | PRNT |
| Fusion protein | 1(BALB/C mice) | 1:80 | 1:160 | ICR mice | 1:320 | 1:300 | 1:160 | 1:80 |
| | 2 | 1:320 | | | 1:1280 | | 1:320 | |
| | 3 | 1:20 | | | 1:320 | | 1:160 | |
| | 4 | 1:80 | | | 1:320 | | 1:160 | |
| | 5 | 1:320 | | | 1:160 | | 1:80 | |
| | 6 | 1:20 | | | | | | |
| | 7 | 1:160 | | | | | | |
| | 8 | 1:20 | | | | | | |
| | 9 | 1:20 | | | | | | |
| | 1(ICR mice Bleed-I) | 1:20 | 1:160 | | | | | |
| | 2 | 1:80 | | | | | | |
| | 3 | 1:40 | | | | | | |
| | 1(ICR mice Bleed-II) | 1:640 | 1:320 | | | | | |
| | 2 | 1:640 | | | | | | |
| | 3 | 1:320 | | | | | | |
| Protein-A | 1(BALB/C mice) | <1:20 | <1:10 | | ND | | ND | |
| | 2 | <1:20 | | | | | | |
| | 3 | <1:20 | | | | | | |
| | 4 | <1:20 | | | | | | |
| | 5 | <1:20 | | | | | | |
| | 6 | <1:20 | | | | | | |
| | 7 | <1:20 | | | | | | |
| | 8 | <1:20 | | | | | | |
| | 9 | <1:20 | | | | | | |
| | 1(ICR mice Bleed-I] | <1:20 | <1:10 | | | | | |
| | 2 | <1:20 | | | | | | |
| | 3 | <1:20 | | | | | | |
| | 1(ICR mice Bleed-II] | <1:20 | <1:10 | | | | | |
| | 2 | <1:20 | | | | | | |
| | 3 | <1:20 | | | | | | |
| DEN-2 virus | 1(BALB/C mice) | 1:320 | 1:320 | | ND | | ND | |
| | 2 | 1:20 | | | | | | |
| | 3 | 1:160 | | | | | | |
| | 4 | 1:320 | | | | | | |
| | 5 | 1:20 | | | | | | |
| | 6 | 1:20 | | | | | | |
| | 7 | 1:160 | | | | | | |
| | 8 | 1:320 | | | | | | |
| NONE | 1(ICR mice) | <1:20 | <1:10 | | <1:20 | | <1:20 | |

[a]HI (Hemagglutination Inhibition) tests performed using sera from individual mice.
[b]PRNT (Plaque Reduction Neutralization Test)-80% assays performed using pooled mouse sera and DEN-2 virus (New Guinea C strain).
[c]Adjuvants used for immunization were Hunter TiterMax (HTM), Aluminum hydroxide (AH) or no adjuvant (NONE).

EXAMPLE 3

Animal Protection Assay

Figure 3:
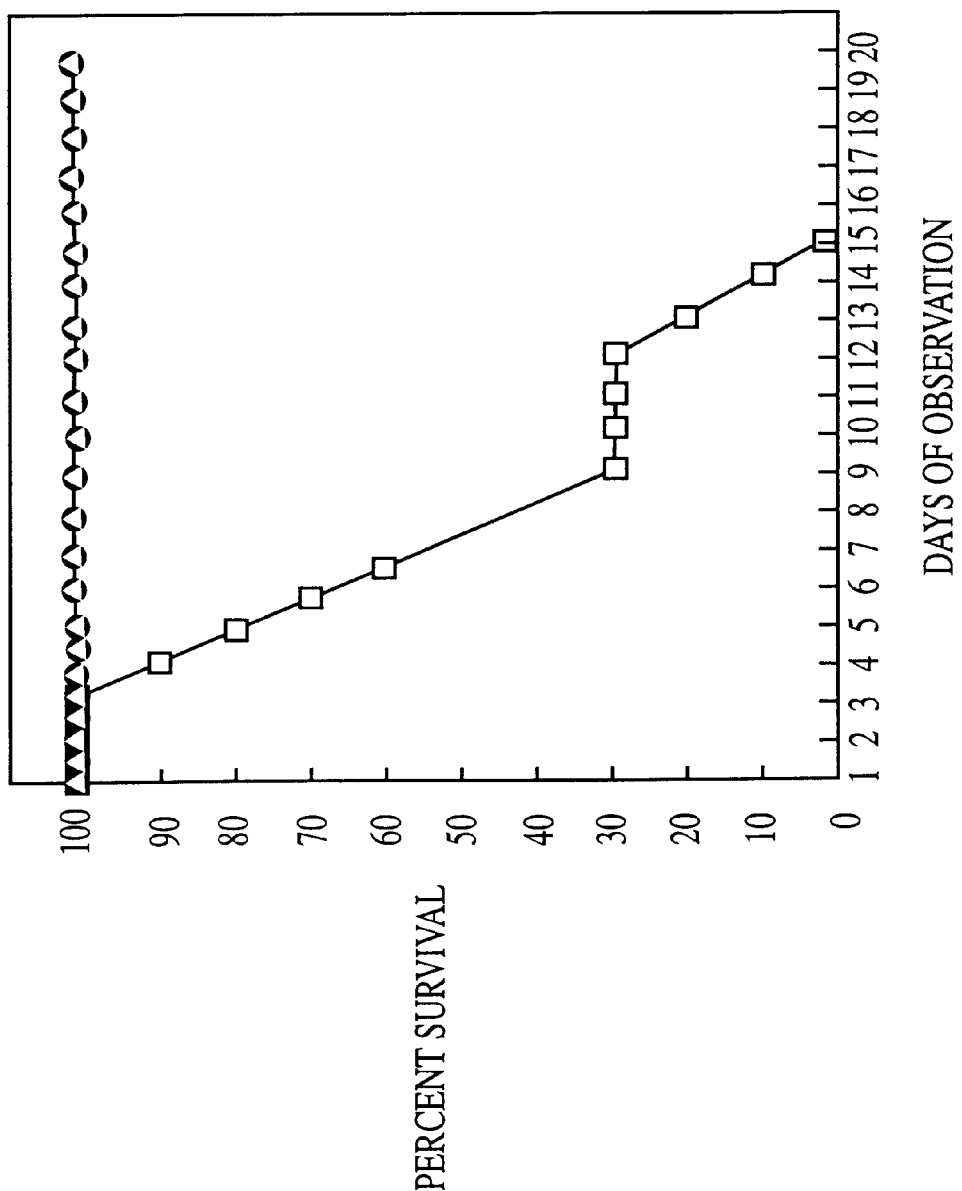
FIG. 3 demonstrates the survival of mice immunized with recombinant DEN-2 antigen. Groups of mice were immunized subcutaneously with either recombinant fusion protein (5 mg×4 doses) (triangle), live DEN-2 virus (solid circle) ($10^6$ PFU), or protein A alone (box) (5 mg×4 doses). Following immunization, mice were challenged by intracranial injection with 100 $LD_{50}$ of live DEN-2 virus. The percent of mice surviving at each day post challenge is shown.

The immune response to recombinant fusion protein was further evaluated in a protection experiment with 3 week-old BALB/C mice. Groups of mice were immunized with purified recombinant fusion protein (9 mice), protein-A alone (10 mice) or with live DEN-2 virus (10 mice). Four inoculations each containing 5 μg of protein were administered over a 3 week period. All mice were bled at 6 weeks of age and then challenged by intracranial (IC) injection of live DEN-2 virus (100 $LD_{50}$) and observed daily for 20 days. Pre-challenge sera from mice immunized with the recombinant fusion protein, and those immunized with live DEN-2 virus showed anti-DEN-2 antibodies in HI tests (up to 1:320) and neutralizing tests (up to 1:160). Control mice immunized with protein-A alone did not exhibit detectable HI (<1:20) or neutralizing (<1:10) antibodies (see Table 1). All mice immunized with recombinant fusion protein, or with DEN-2 virus survived after IC challenge with virulent DEN-2 virus; there were no survivors among mice immunized with the protein-A control (FIG. 3).

These results show that an E. coli-expressed fusion protein containing AA 288 to 491 from the C-terminus of E glycoprotein and the first 65 AA of NS1 of DEN-2 virus fused to Staphylococcal protein-A can immunize mice against DEN-2 virus. Mice immunized with the purified, recombinant fusion protein responded with anti-DEN-2 neutralizing and HI antibodies. The antibody titers were similar to those seen in mice after infection with DEN-2 virus. Immunized mice were solidly protected against lethal intracranial challenge with DEN-2 virus. These results, like those previously reported for a recombinant JE virus fusion protein (Srivastava, A. K. et al. *Microbiol. Immunol* 1991, 35, 863–870), demonstrate that it may be feasible to make flavivirus vaccines in E. coli.

The high titers of anti-DEN-2 virus neutralizing antibody elicited in mice by this recombinant immunogen appear to distinguish it from most other recombinant DEN subunit immunogens. It appears that our immunogen contains one or more virus neutralization epitopes which are presented to the murine immune system in an immunologically "correct" conformation. How many epitopes it contains is not known, however, it does contain a recognition site for at least one anti-DEN-2 N MAb, 3H5, a part of which is specified by AA 384–396 of E protein (Trirawatanapong, T. et al. *Gene* 1992, 116, 139–150). This MAb reacted with our recombinant in a Western blot assay.

One important feature of our fusion protein with protein-A may be its solubility which made it easy to purify by IgG-affinity chromatography, thus avoiding denaturing methods which might result in loss of immunogenicity. The role of the protein-A moiety in maintaining solubility is not clear, but a similar JE fusion protein with TrpE was insoluble, and after purification on SDS-polyacrylamide gels was an ineffective immunogen in mice. It was speculated that this was due to incorrect conformation or presentation of the antigen to the immune system. Other possible roles for the protein-A component might be to effect antigen presentation, perhaps by potentiating binding to Ig-bearing macrophages and B-cells, or to serve as an adjuvant. Interestingly, both HTM and AH adjuvants significantly improved the immunogenicity of the recombinant protein; however, AH has the advantage of already being approved for human use. Another critical feature of our immunogen may be the presence of the short NS1 protein sequence, the role of which in protection is unclear.

Immunogenicity of Dengue-2 Fusion Protein in Rhesus Monkeys

Adult Rhesus monkeys were immunized with various dilutions of purified fusion protein with alum. Two inoculations were given, spaced one month apart. Sera obtained two weeks after the second inoculation were tested for HI antibodies (Table 2). After the second inoculation, two of three animals responded with HI antibodies.

TABLE 2

Anti-DEN-2 antibody titers in sera from monkeys immunized with recombinant DEN-2 fusion protein.

| S.No. | Immunogen | Adjuvant | HI titer |
|---|---|---|---|
| 1. | 100.0 ug | ALUM | 1:40 |
| 2. | 100.0 ug | ALUM | 1:80 |
| 3. | 100.0 ug | ALUM | <1:10 |
| 4. | 33.3 ug | ALUM | <1:10 |
| 5. | 33.3 ug | ALUM | <1:10 |
| 6. | 33.3 ug | ALUM | <1:10 |
| 7. | 10.0 ug | ALUM | <1:10 |
| 8. | 10.0 ug | ALUM | <1:10 |
| 9. | 10.0 ug | ALUM | <1:10 |

These results indicate that a higher HI and neutralizing antibody titer, and protection against dengue virus challenge, may be elicited after a third dose of fusion protein immunogen.

In future experiments, we will attempt to assess the role of protein-A by removing it by endopeptidase treatment of the fusion protein after its purification. Similarly, the role of NS1 sequences will be assessed by their removal from the gene fragment prior to expression. In this way we hope to elucidate the critical elements in the system, and hopefully pave the way for a candidate recombinant subunit vaccine against DEN virus.

What is claimed is:

1. A method for the diagnosis of dengue virus disease comprising the steps of:
   (i) coating a surface with a recombinant fusion protein consisting essentially of amino acids corresponding to a DNA sequence of SEQ ID NO: 1 or an allelic variation thereof which encodes a protein which maintains the neutralizing antibody production characteristic of the recombinant protein;
   (ii) contacting said coated surface with serum from an individual suspected of having said disease;
   (iii) detecting the presence or absence of the disease by detecting the presence or absence of a complex formed between said recombinant protein and antibodies specific therefor present in said serum, wherein presence of the complex is indicative of the presence of disease in the individual.

2. A dengue virus diagnostic kit comprising a recombinant fusion protein consisting essentially of amino acids corresponding to a DNA sequence specified in SEQ ID NO:1 or an allelic variation thereof which encodes a protein which maintains the neutralizing antibody production characteristic of the recombinant protein, and ancillary reagents suitable for use in detecting the presence or absence of antibodies to said recombinant protein in a mammalian serum or tissue sample.

3. A method for the diagnosis of dengue virus disease comprising the steps of:
 (i) coating a surface with a recombinant protein consisting essentially of the sequence specified in SEQ ID NO: 2 or an allelic variation thereof which maintains the neutralizing antibody production characteristics of the recombinant protein;
 (ii) contacting said coated surface with serum from an individual suspected of having said infection;
 (iii) detecting the presence or absence of the disease by detecting the presence or absence of a complex formed between said recombinant protein and antibodies specific therefor present in said serum wherein presence of the complex is indicative of the presence of disease in the individual.

4. A dengue virus diagnostic kit comprising a recombinant protein consisting essentially of the sequence specified in SEQ ID NO:2 or an allelic variation thereof which maintains the neutralizing antibody production characteristics of the recombinant protein, and ancillary reagents suitable for use in detecting the presence of antibodies to said recombinant protein in a mammalian serum or tissue sample.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
(A) LENGTH: 815 base pairs
(B) TYPE: Nucleic acid
(C) STRANDEDNESS: Single
(D) TOPOLOGY: Linear (ii) SEQUENCE DESCRIPTION: SEQ ID NO:1:

```
ATGGACAAAT  TACAACTTAA  AGGGATGTCA  TACTCCATGT                        40

GCACAGGAAA  GTTTAAAGTT  GTGAAGGAAA  TAGCAGAAAC                        80

ACAACATGGA  ACAATAGTCA  TTAGAGTACA  ATATGAAGGA                       120

GACGGCTCTC  CATGCAAGAC  CCCTTTTGAG  ATAATGGATC                       160

TGGAAAAAAG  ACATGTTTTG  GGCCGCCTGA  CCACAGTCAA                       200

CCCAATTGTA  ACAGAAAAGG  ACAGTCCAGT  CAACATAGAA                       240

GCAGAACCTC  CATTCGGAGA  CAGCTACATC  ATCATAGGAC                       280

TGGAACCAGG  ACAATTGAAG  CTGGACTGGT  TCAAGAAAGG                       320

AAGTTCCATC  GGCCAAATGT  TTGAGACAAC  AATGAGGGGA                       360

GCGAAAAGAA  TGGCCATTTT  GGGCGACACA  GCCTGGGATT                       400

TTGGATCTCT  GGGAGGAGTG  TTCACATCAA  TAGGAAAGGC                       440
```

```
TCTCCACCAG   GTTTTTGGAG   CAATCTACGG   GGCTGCTTTC                    480

AGTGGGGTCT   CATGGACTAT   GAAGATCCTC   ATAGGAGTTA                    520

TCATCACATG   GATAGGAATG   AACTCACGTA   GCACATCACT                    560

GTCTGTGTCA   CTGGTATTAG   TGGGAATCGT   GACACTGTAC                    600

TTGGGAGTTA   TGGTGCAGGC   CGATAGTGGT   TGCGTTGTGA                    640

GCTGGAAGAA   CAAAGAACTA   AAATGTGGCA   GTGGAATATT                    680

CGTCACAGAT   AACGTGCATA   CATGGACAGA   ACAATACAAG                    720

TTCCAACCAG   AATCCCCTTC   AAAACTGGCT   TCAGCCATCC                    760

AGAAAGCTCA   TGAAGAGGGC   ATCTGTGGAA   TCCGCTCAGT                    800

AACAAGACTG   GAAAA                                                   815
```

(2) INFORMATION FOR SEQ ID NO:2:

(i) SEQUENCE CHARACTERISTICS:
        (A) LENGTH: 271 amino acids
        (B) TYPE: amino acid
        (C) TOPOLOGY: Linear (ii) SEQUENCE DESCRIPTION: SEQ ID NO: 2:

```
Met Asp Lys Leu Gln Leu Lys Gly Met Ser Tyr Ser Met Cys Thr
 1               5                  10                  15

Gly Lys Phe Lys Val Val Lys Glu Ile Ala Glu Thr Gln His Gly
                20                  25                  30

Thr Ile Val Ile Arg Val Gln Tyr Glu Gly Asp Gly Ser Pro Cys
                35                  40                  45

Lys Thr Pro Phe Glu Ile Met Asp Leu Glu Lys Arg His Val Leu
                50                  55                  60

Gly Arg Leu Thr Thr Val Asn Pro Ile Val Thr Glu Lys Asp Ser
                65                  70                  75

Pro Val Asn Ile Glu Ala Glu Pro Pro Phe Gly Asp Ser Tyr Ile
                80                  85                  90

Ile Ile Gly Val Glu Pro Gly Gln Leu Lys Leu Asp Trp Phe Lys
                95                 100                 105

Lys Gly Ser Ser Ile Gly Gln Met Phe Glu Thr Thr Met Arg Gly
               110                 115                 120

Ala Lys Arg Met Ala Ile Leu Gly Asp Thr Ala Trp Asp Phe Gly
               125                 130                 135

Ser Leu Gly Gly Val Phe Thr Ser Ile Gly Lys Ala Leu His Gln
               140                 145                 150

Val Phe Gly Ala Ile Tyr Gly Ala Ala Phe Ser Gly Val Ser Trp
               155                 160                 165

Thr Met Lys Ile Leu Ile Gly Val Ile Ile Thr Trp Ile Gly Met
               170                 175                 180

Asn Ser Arg Ser Thr Ser Leu Ser Val Ser Leu Val Leu Val Gly
               185                 190                 195

Ile Val Thr Leu Tyr Leu Gly Val Met Val Gln Ala Asp Ser Gly
               200                 205                 210

Cys Val Val Ser Trp Lys Asn Lys Glu Leu Lys Cys Gly Ser Gly
               215                 220                 225

Ile Phe Val Thr Asp Asn Val His Thr Trp Thr Glu Gln Tyr Lys
               230                 235                 240

Phe Gln Pro Glu Ser Pro Ser Lys Leu Ala Ser Ala Ile Gln Lys
```

```
                        245                 250                 255
Ala His Glu Glu Gly Ile Cys Gly Ile Arg Ser Val Thr Arg Leu
                260                 265                 270

Glu
271

(2) INFORMATION FOR SEQ ID NO: 3:

(i) SEQUENCE CHARACTERISTICS:
        (A) LENGTH: 31 base pairs
        (B) TYPE:  Nucleic Acid
        (C) STRANDEDNESS: Double
        (D) TOPOLOGY: Linear (ii) SEQUENCE DESCRIPTION: SEQ ID NO: 3:

TGACAGATCT  ATGATGGCCG  ACATCCGTGC  A                                31

(2) INFORMATION FOR SEQ ID NO: 4:

(i) SEQUENCE CHARACTERISTICS:
        (A) LENGTH: 36 base pairs
        (B) TYPE:  Nucleic Acid
        (C) STRANDEDNESS: Double
        (D) TOPOLOGY: Linear (ii) SEQUENCE DESCRIPTION: SEQ ID NO: 4:

GCGACTTATG  CTGCAGGCCG  ATAGTGGTTG  CGTTGT                           36

(2) INFORMATION FOR SEQ ID NO: 5:

(i) SEQUENCE CHARACTERISTICS:
        (A) LENGTH: 24 base pairs
        (B) TYPE:  Nucleic Acid
        (C) STRANDEDNESS: Double
        (D) TOPOLOGY: Linear (ii) SEQUENCE DESCRIPTION: SEQ ID NO: 5:

GCAGGCCGAT  AGTGGTTGCG  TTGT                                         24

(2) INFORMATION FOR SEQ ID NO: 6:

(i) SEQUENCE CHARACTERISTICS:
        (A) LENGTH: 29 base pairs
        (B) TYPE:  Nucleic Acid
        (C) STRANDEDNESS: Double
        (D) TOPOLOGY: Linear (ii) SEQUENCE DESCRIPTION: SEQ ID NO: 6:

TACTGCAGTT  AACCCACCAT  AACCATCAC                                    29

(2) INFORMATION FOR SEQ ID NO: 7:

(i) SEQUENCE CHARACTERISTICS:
        (A) LENGTH: 35 base pairs
        (B) TYPE:  Nucleic Acid
        (C) STRANDEDNESS: Double
        (D) TOPOLOGY: Linear (ii) SEQUENCE DESCRIPTION: SEQ ID NO: 7:

ACAACGCAAC  CACTATCGGC  CTGCACCATA  ACTCC                            35

(2) INFORMATION FOR SEQ ID NO: 8:

(i) SEQUENCE CHARACTERISTICS:
        (A) LENGTH: 24 base pairs
        (B) TYPE:  Nucleic Acid
```

```
            (C) STRANDEDNESS: Double
            (D) TOPOLOGY: Linear (ii) SEQUENCE DESCRIPTION: SEQ ID NO: 8:

GCAGGCCGAT  AGTGGTTGCG  TTGT                                              24

(2) INFORMATION FOR SEQ ID NO: 9:

(i) SEQUENCE CHARACTERISTICS:
            (A) LENGTH: 27 base pairs
            (B) TYPE:  Nucleic Acid
            (C) STRANDEDNESS: Double
            (D) TOPOLOGY: Linear (ii) SEQUENCE DESCRIPTION: SEQ ID NO: 9:

CCCGGGATGA  TGGACAAATT  ACAACTT                                           27

(2) INFORMATION FOR SEQ ID NO: 10:

(i) SEQUENCE CHARACTERISTICS:
            (A) LENGTH: 27 base pairs
            (B) TYPE:  Nucleic Acid
            (C) STRANDEDNESS: Double
            (D) TOPOLOGY: Linear (ii) SEQUENCE DESCRIPTION: SEQ ID NO: 10:

GTCGACTTAA  TTTTCCAGTC  TTGTCAT                                           27

(2) INFORMATION FOR SEQ ID NO: 11:

(i) SEQUENCE CHARACTERISTICS:
            (A) LENGTH: 15 base pairs
            (B) TYPE:  Nucleic Acid
            (C) STRANDEDNESS: Double
            (D) TOPOLOGY: Linear (ii) SEQUENCE DESCRIPTION: SEQ ID NO: 11:

GTCCAAGTTT  CCCTG                                                         15

(2) INFORMATION FOR SEQ ID NO: 12:

(i) SEQUENCE CHARACTERISTICS:
            (A) LENGTH: 17 base pairs
            (B) TYPE:  Nucleic Acid
            (C) STRANDEDNESS: Double
            (D) TOPOLOGY: Linear (ii) SEQUENCE DESCRIPTION: SEQ ID NO: 12:

AATGATAACC  ATCTCGC                                                       17
```